United States Patent [19]
Nakagawa et al.

[11] Patent Number: 5,467,635
[45] Date of Patent: Nov. 21, 1995

[54] GAS CHROMATOGRAPH

[75] Inventors: Kazuya Nakagawa, Kyoto; Toyoaki Fukushima, Uji, both of Japan

[73] Assignee: Shimadzu Corporation, Japan

[21] Appl. No.: 354,789

[22] Filed: Dec. 12, 1994

[51] Int. Cl.$^6$ ............................ B01D 15/08; G01N 30/88
[52] U.S. Cl. ................................. 73/23.350; 73/23.420; 95/19; 422/89; 422/99
[58] Field of Search .................... 73/23.35, 23.42; 55/18; 95/19, 22; 422/89, 99

[56] References Cited

U.S. PATENT DOCUMENTS

| | | | |
|---|---|---|---|
| 3,171,274 | 3/1965 | Loyd | 73/23.1 |
| 3,798,973 | 3/1974 | Estey | 73/422 GC |
| 4,035,168 | 7/1977 | Jennings | 55/67 |
| 4,230,464 | 10/1980 | Bonmati et al. | 55/23 |
| 4,976,750 | 12/1990 | Munari | 55/21 |
| 4,994,096 | 2/1991 | Klein et al. | 55/20 |
| 5,108,466 | 4/1992 | Klein et al. | 55/20 |
| 5,339,673 | 8/1994 | Nakagawa et al. | 73/23.36 |

FOREIGN PATENT DOCUMENTS

| | | | |
|---|---|---|---|
| 570707 | 11/1993 | European Pat. Off. | 73/23.35 |
| 4431077 | 12/1969 | Japan | 73/23.35 |
| 57-13329 | 3/1982 | Japan | 95/19 |
| 6235612 | 11/1985 | Japan | 95/22 |

Primary Examiner—Hezron E. Williams
Assistant Examiner—J. David Wiggins
Attorney, Agent, or Firm—Oliff & Berridge

[57] ABSTRACT

A target pressure is calculated by a fluid dynamic theory using a length of the column, an inner diameter of the column and the temperature of the column so that the linear velocity of the gas flowing through the column is at a preset pre-determined value at which the HETP (height equivalent to a theoretical plate) value, as calculated from chemical kinematic theory, is the minimum and the resolution of the column is the highest. Then the pressure of the gas at the entrance of the column of a chromatograph is maintained at the calculated target pressure while the temperature of the column is raised to reduce the analyzing time.

12 Claims, 2 Drawing Sheets

GAS CHROMATOGRAPH

The present invention relates to a gas chromatograph.

BACKGROUND OF THE INVENTION

A temperature controlled analysis (or a temperature-program-controlled analysis) is often used to reduce the duration of an analysis of a gas chromatograph. In the temperature controlled analysis, the temperature of the column of the chromatograph is gradually raised, whereby the speed of the gas flowing through the column decreases because of increase in the flow resistance of the column, though there is a minor opposing factor that the volume of the gas increases as the temperature rises. Therefore, the pressure of the gas is increased as the temperature is raised in order to compensate for the decrease in the speed of the gas.

There is an index called Height Equivalent to a Theoretical Plate (HETP) which represents the resolution of a column of a chromatograph. The value H of HETP is defined as $$H=L/N,$$

where L is the length of a column and N is the theoretical number of plates of the column, and is calculated from a chemical kinematic theory as $$H=B/v+(C_G+C_L)\cdot v,$$

$$B=2\cdot D_G\cdot(1/j),$$

$$C_G=[(1+6\cdot k+11\cdot k^2)/\{2^4\cdot(1+k)^2\}]\cdot(r^2/D_G)\cdot(1/j)$$

$$C_L=2\cdot k/\{3\cdot(1+k)^2\}\cdot(d_f^2/D_L)$$

$$j=(3/2)\cdot(P^2-1)/(P^3-1)$$

$$P=Pi/Po$$

$$k=(C_S\cdot V_S)/(C_M\cdot V_M)$$

where $D_G$ is the diffusion coefficient of the sample in the gas phase. $D_L$ is the diffusion coefficient of the sample in the liquid static phase, r is the inner radius of the column, $d_f$ is the thickness of the liquid static phase layer, k is the capacity ratio, $C_S$ and $C_M$ are the concentrations of the sample in the static phase and in the mobile phase, $V_S$ and $V_M$ are the volumes of the sample in the static phase and in the mobile phase, and Pi and Po are pressures of the carrier gas at the entrance and at the exit of the column. According to the above equations, the value H of HETP changes as shown in FIG. 3 with respect to the linear velocity v of the carrier gas flowing through the column, and there is the minimum in the HETP value at a certain linear velocity $v_m$ where the resolution is the highest. When P is approximately 1, the linear velocity $v_m$ at which the HETP value is minimum is approximated as $$v_m=\{B/(C_G+C_L)\}^{1/2}.$$

A problem in the conventional gas chromatograph is that, in controlling the pressure of the gas to compensate for the decrease in the gas flow due to the temperature rise, the linear velocity of the gas is not regarded but the rate of the mass flow of the gas is aimed to be constant. Therefore the resolution is not always highest in the conventional gas chromatograph though the analyzing time is reduced.

SUMMARY OF THE INVENTION

The present invention addresses the highest resolution of the gas chromatograph as well as the analyzing speed. Thus the gas chromatograph according to the present invention comprises:

a pressure regulator for regulating a pressure of a gas at an entrance of a column of the gas chromatograph;

a pressure sensor for detecting a pressure of the gas at the entrance of the column;

calculating means for calculating a target pressure of the gas at the entrance of the column from a length of the column, an inner diameter of the column and a temperature of the column, the target pressure being such a pressure that a linear velocity of the gas flowing through the column is at a preset pre-determined value; and a controller for controlling the pressure regulator so that the pressure detected by the pressure sensor is maintained at the target pressure.

The linear velocity of the gas flowing through the column is calculated by a fluid dynamic theory using: the length L and inner diameter D of the column; the viscosity of the gas; and the pressure of the gas at the entrance of the column. Of course it is possible to add a correcting factor derived from experiments to obtain more exact linear velocity. Since the viscosity of the gas is determined by its temperature depending on the kind of the gas, the linear velocity is obtained from: the length L and inner diameter D of the column; the temperature of the gas; and the pressure of the gas at the entrance of the column. Thus, the pressure of the gas at the entrance of the column is inversely calculated from: the length L and inner diameter D of the column; the temperature of the gas; and the linear velocity of the gas in the column. The calculating means perform this calculation using: the temperature of the column (which is regarded to be equal to the temperature of the gas); the value of the linear velocity $v_m$ at which the HETP value is the minimum (i.e., at which the resolution of the column is the highest); and the values of the length L and inner diameter D of the column used. The temperature of the column may be actually measured or it may be taken from the value of the temperature program at every time point if the column temperature is controlled. The pressure at the entrance of the column is maintained at the calculated pressure $P_m$ by the controller whereby the linear velocity of the gas flowing through the column is maintained at the value $v_m$ where the HETP value is the minimum and the resolution of the column is the highest.

DETAILED DESCRIPTION OF PREFERRED EMBODIMENTS

Figure 1:
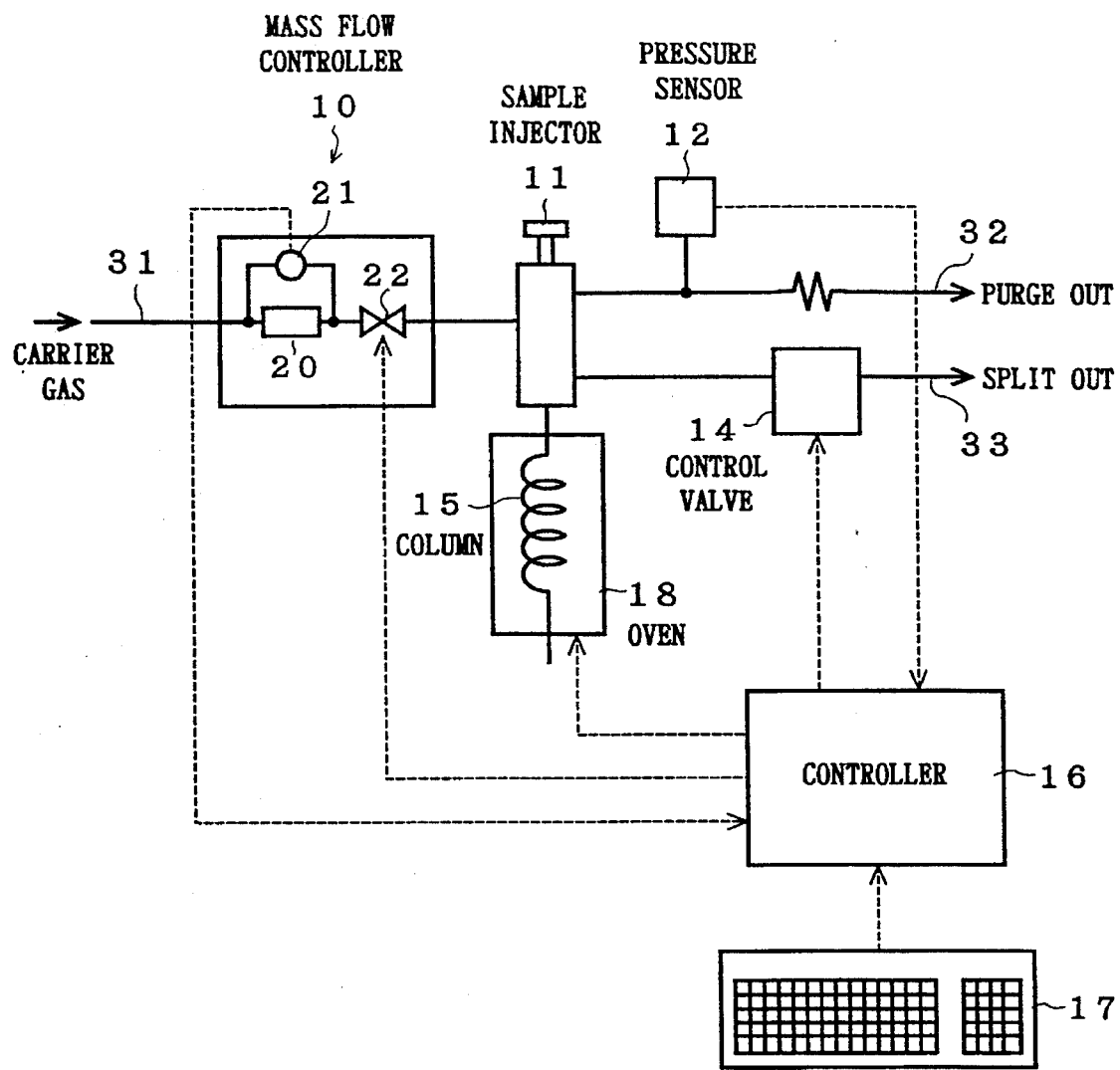
FIG. 1 is a gas flow diagram of a split type gas chromatograph of the first embodiment.

A split type gas chromatograph is described with reference to FIG. 1 as the first embodiment of the present invention. The gas flow system of the gas chromatograph of the present embodiment is composed of a sample injector 11, a column 15, a carrier gas line 31, a purge out line 32, and a split out line 33.

The carrier gas line 31 connects the sample injector 11 to a carrier gas source (not shown), on which a mass flow controller 10 is provided for controlling the mass flow rate U of the carrier gas. The mass flow controller 10 includes: a laminar flow element 20 and a differential pressure sensor 21 for detecting the flow rate of the carrier gas; and a flow regulating valve 22 for regulating the flow of the carrier gas. The split out line 33 connects the sample injector 11 to the outer atmosphere to discharge a part of (usually a large part of) the sample injected in the sample injector 11 to be flown through the column 15. On the split out line 33 is provided a control valve 14 for controlling the amount of gas flowing through the split out line 33. The purge out line 32 connects the sample injector 11 to the outer atmosphere and its end is attached at a neighbor of the injecting port of the sample injector 11 to purge out the vapor of a septum (a rubber cap) of the injecting port. A pressure sensor 12 is provided on the purge out line 32. Since there is little flow resistance between the pressure sensor 12 and the sample injector 11, the pressure detected by the pressure sensor 12 is regarded as the pressure in the sample injector 11 or the pressure at the entrance of the column 15.

Figure 3:
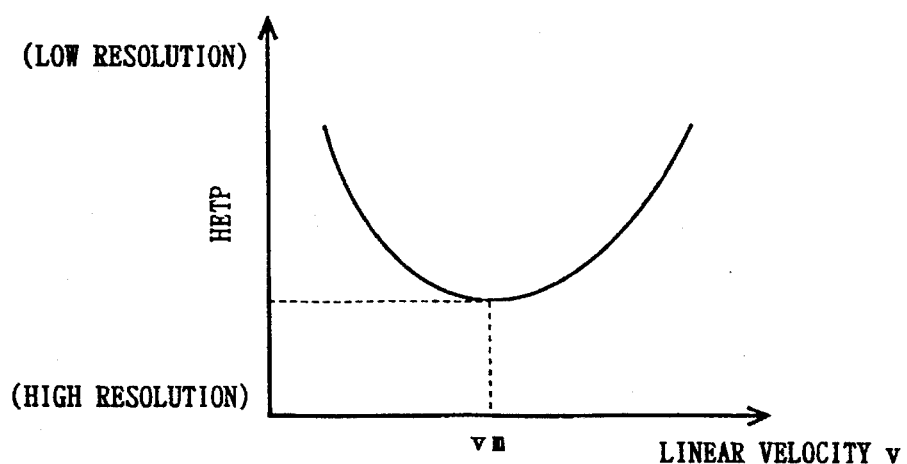
FIG. 3 is a graph showing the relationship between the HETP value and the linear velocity.

An oven 18 is furnished around the column 15 whose temperature is controlled according to a preset program by a controller 16. The controller 16 of the present embodiment not only controls the temperature of the oven 18, but it also controls the pressure P at the entrance of the column 15 so that the linear velocity v of the gas flowing through the column 15 is always maintained at a value $v_m$ while the temperature changes. The target value $v_m$ of the linear velocity v is set at the minimum value of the HETP (i.e., at the highest resolution of the chromatograph) as shown in FIG. 3.

The linear velocity v of the gas flowing through the column 15 can be calculated by a fluid dynamic theory using the length L and the inner diameter D of the column 15, the viscosity μ of the gas, and the pressure of the gas at the entrance of the column 15, as $$v = f(D, L, \mu, P).$$

Thus the pressure P can be calculated from the length L and the inner diameter D of the column 15, the viscosity μ of the gas, and the linear velocity v, as $$P = g(D, L, \mu, v).$$

The term $g(D, L, \mu, v)$ can be approximated as follows.

$$P = (L/D^2) \cdot \mu \cdot \{a \cdot (L/D^2) \cdot \mu \cdot v + b\} \cdot v \quad (1)$$

where a and b are constants.

The viscosity μ of the gas flowing through the column 15 changes with respect to the absolute temperature T as follows.

$$\mu = \alpha \cdot \{(T_{20} + \beta)/(T + \beta)\} \cdot (T/T_{20})^{3/2} \quad (2)$$

where $T_{20} = 273 + 20$ (K), and α and β are constants. In a rather restricted temperature range, equation (2) can be approximated linearly as follows.

$$\mu = \gamma \cdot T + \delta \quad (3)$$

The constants a, b, γ and δ (or α and β) can be obtained by putting measured values selected from the rather restricted temperature range into those variables in the above equations. For example, an actual form of equation (1) is, $$P = (L/D^2) \cdot \mu \cdot \{4.05 \times 10^{-3} \times (L/D^2) \cdot \mu \cdot v + 3.3\} \cdot v \quad (11)$$

(in cgs unit), and equation (3) is, $$\begin{aligned} \mu &= 0.0412 \times T + 18.70 \text{ (for He)} \\ &= 0.0355 \times T + 17.24 \text{ (for Ne)} \\ &= 0.0159 \times T + 8.73 \text{ (for H}_2\text{)} \\ &= 0.0492 \times T + 22.02 \text{ (for Ar)}. \end{aligned} \quad (31)$$

The controller 16 maintains the linear velocity $v_m$ of the gas as follows while performing the temperature-program control. First, it receives data of the length L and inner diameter D of the column 15 from the keyboard 17 or from an external memory device (not shown), and stores the data into a RAM. Then an analyzing operation is started. The temperature T(t) of the oven 18 is controlled according to a preset temperature program, and the viscosity μ(t) of the gas at every time point t is calculated by putting the value of temperature T(t) at the time point t into equation (31). The value of the viscosity μ=μ(t) thus calculated and the values of L, D, v=$v_m$ stored in the RAM are put into equation (11) to obtain the gas pressure P(t) at the entrance at the time point t.

Then the control valve 14 is controlled so that the column entrance pressure P detected by the pressure sensor 12 becomes equal to the calculated value P(t), whereby the linear velocity v of the gas flowing through the column 15 is maintained at the optimal value $v_m$ at which the HETP value is the minimum (or the resolution is the highest) throughout the temperature-program-controlled gas chromatographic operation.

While the temperature of the oven 18 and the pressure or target value at the column entrance are thus controlled, the controller 16 further controls the mass flow controller 10 to maintain the split ratio constant. The mass flow rate Vc of the column 15 can be calculated from the length L and inner diameter D of the column 15, the linear velocity $v_m$ and the pressure P(t). The mass flow rate Vs of the split out line 33 is calculated from the mass flow rate Vc of the column 15 and a given split ratio S. Then the total mass flow rate Vt is calculated by adding the column mass flow rate Vc and the split mass flow rate Vs. The mass flow controller 10 is controlled so that the rate of the gas flowing through the mass flow controller 10 is maintained at the total mass flow rate Vt, whereby the split ratio is maintained at the given ratio S while the linear velocity v is maintained at $v_m$.

In the above embodiment, the length L and inner diameter D of the column 15 used were given by the operator from the keyboard 17. A more convenient way is that several sets of such data as corresponding to different columns are stored in the memory of the controller 16 beforehand and a corresponding data set is retrieved from the memory when the operator designates a column A. Similar system can be used for inputting different values of the viscosity μ(t) of the carrier gas.

Figure 2:
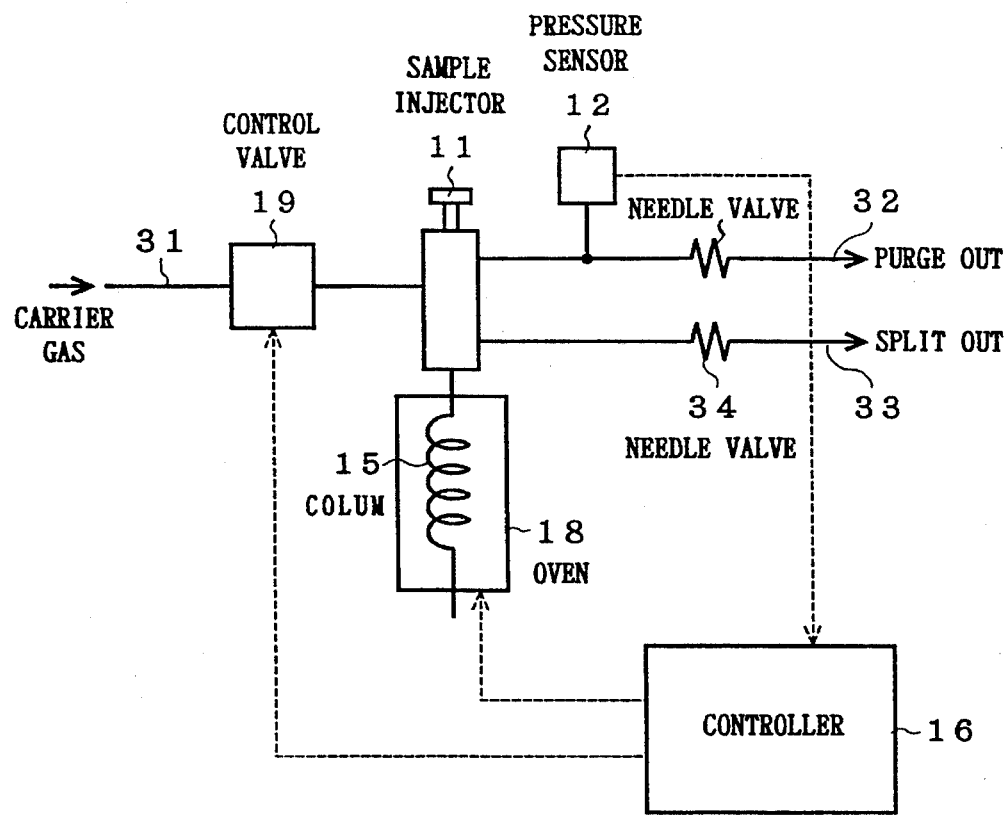
FIG. 2 is a gas flow diagram of another embodiment.

The second embodiment of the present invention is shown in FIG. 2, in which the pressure P(t) at the entrance of the column 15 is controlled not on the split out line 33 as in the first embodiment but on the carrier gas line 31. That is, a control valve 19 is provided on the carrier gas line 31 and the controller 16 controls the control valve 19 to maintain the pressure at the calculated value P(t). In the present embodiment, a needle valve is provided on the split out line 33 and the needle valve is controlled in a split mode analysis. When the needle valve is completely shut (or by eliminating the split out line 33 itself), a wide bore injection (WBI) analysis can be performed, in which the entire amount of sample injected is sent to the column 15.

What is claimed is:

1. A gas chromatograph comprising:

a pressure regulator under variable control via electrical input signals for regulating a pressure of a gas at an entrance of a column of the gas chromatograph;

a pressure sensor for detecting a pressure of the gas at the entrance of the column;

calculating means for calculating a target pressure of the gas at the entrance of the column from a length of the column, an inner diameter of the column and a temperature of the column, the target pressure being such a pressure that a linear velocity of the gas flowing through the column is at a preset pre-determined value; and a controller with electrical output signals for controlling the pressure regulator so that the pressure detected by the pressure sensor is maintained at the target pressure.

2. The gas chromatograph according to claim 1, wherein the gas chromatograph further comprises temperature controlling means for controlling the temperature of the column according to a preset temperature program that serves to reduce the analyzing time.

3. The gas chromatograph according to claim 2, wherein the preset pre-determined value of the linear velocity is a value at which a HETP (height equivalent to a theoretical plate) value is the minimum where said HETP value corresponds to maximum chromatographic resolution.

4. The gas chromatograph according to claim 3, wherein the target pressure P is calculated by the following formulae:

$$P=(L/D^2)\cdot\mu\cdot\{a\cdot(L/D^2)\cdot\mu\cdot v_m+b\}\cdot v_m$$

$$\mu=\alpha\cdot\{(T_{20}+\beta)/(T+\beta)\}\cdot(T/T_{20})^{3/2}$$

where L is the length of the column, D is the inner diameter of the column, T is the absolute temperature of the column, is the viscosity of gas flowing thru the column, a and b and $\alpha$ and $\beta$ are constants to be determined for a particular column and gas, $T_{20}$ is 293 degrees Kelvin scale, and $v_m$ is the preset pre-determined value of the linear velocity of the gas at which the HETP value is the minimum.

5. The gas chromatograph according to claim 4, wherein the values of $\mu$ at a plurality of temperature values T of the column and for a plurality of gases are calculated and stored in a memory beforehand, and an appropriate value of $\mu$ is retrieved from the memory in an analysis.

6. The gas chromatograph according to claim 3, wherein the target pressure P is calculated by the following formulae:

$$P=(L/D^2)\cdot\mu\cdot\{a\cdot(L/D^2)\cdot\mu\cdot v_m+b\}\cdot v_m$$

$$\mu=\gamma\cdot T+\delta$$

where L is the length of the column, D is the inner diameter of the column, T$\mu$ is the viscosity of gas flowing thru the column, a and b and $\gamma$ and $\delta$ are constants to be determined for a particular column and gas, $v_{111}$ is the preset pre-determined value of the linear velocity of the gas at which the HETP value is the minimum, and T is the absolute temperature of the column.

7. A method of performing an analysis using a chromatograph including a column, the method comprising the steps of:

calculating a target pressure of a gas at an entrance of the column from a length of the column, an inner diameter of the column and a temperature of the column, the target pressure being such a pressure that a linear velocity of the gas flowing through the column is at a preset pre-determined value; and controlling the pressure at the entrance of the column to be maintained at the target pressure.

8. The gas chromatographic analyzing method according to claim 7, wherein a temperature of the column is controlled according to a preset temperature program that serves to reduce the analyzing time.

9. The gas chromatographic analyzing method according to claim 8, wherein the preset pre-determined value of the linear velocity is a value at which a HETP (height equivalent to a theoretical plate) value is the minimum where said HETP value corresponds to maximum chromatographic resolution.

10. The gas chromatographic analyzing method according to claim 9, wherein the target pressure P is calculated by the following formulae:

$$P=(L/D^2)\cdot\mu\cdot\{a\cdot(L/D^2)\cdot\mu\cdot v_m+b\}\cdot v_m$$

$$\mu=\alpha\cdot\{(T_{20}+\beta)/(T+\beta)\}\cdot(T/T_{20})^{3/2}$$

where L is the length of the column, D is the inner diameter of the column, T is the absolute temperature of the column, $\mu$ is the viscosity of gas flowing thru the column, a and b and $\alpha$ and $\beta$ are constants to be determined for a particular column and gas $T_{20}$ is 293 degrees Kelvin scale, and $v_m$ is the preset pre-determined value of the linear velocity of the gas at which the HETP value is the minimum.

11. The gas chromatographic analyzing method according to claim 10, wherein the values of $\mu$ at a plurality of temperature values T of the column and for a plurality of gases are calculated and stored in a memory beforehand, and an appropriate value of $\mu$ is retrieved from the memory in an analysis.

12. The gas chromatographic analyzing method according to claim 9, wherein the target pressure P is calculated by the following formulae:

$$P=(L/D^2)\cdot\mu\cdot\{a\cdot(L/D^2)\cdot\mu\cdot v_m+b\}\cdot v_m$$

$$\mu=\gamma\cdot T+\delta$$

where L is the length of the column, D is the inner diameter of the column, $\mu$ is the viscosity of gas flowing thru the column, a and b and $\gamma$ and $\delta$ are constants to be determined for a particular column and gas, $v_{111}$ is the preset pre-determined value of the linear velocity of the gas at which the HETP value is the minimum, and T is the absolute temperature of the column.

* * * * *